(12) United States Patent
Depierro et al.

(10) Patent No.: US 10,273,254 B2
(45) Date of Patent: Apr. 30, 2019

(54) PROCESS FOR PREPARING AN ACRYLOYLOXYSILANE

(71) Applicant: Dow Corning Corporation, Midland, MI (US)

(72) Inventors: Michael A Depierro, Midland, MI (US); Marc Halpern, Blackwood, NJ (US); Thomas J Jackson, Midland, MI (US); Karen J Kloet, Midland, MI (US); Aaron R Sprague, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/567,272

(22) PCT Filed: Jun. 17, 2016

(86) PCT No.: PCT/US2016/038069
§ 371 (c)(1),
(2) Date: Oct. 17, 2017

(87) PCT Pub. No.: WO2016/205642
PCT Pub. Date: Dec. 22, 2016

(65) Prior Publication Data
US 2018/0155371 A1    Jun. 7, 2018

Related U.S. Application Data

(60) Provisional application No. 62/182,169, filed on Jun. 19, 2015.

(51) Int. Cl.
    *C07F 7/20*     (2006.01)
    *C07F 7/18*     (2006.01)

(52) U.S. Cl.
    CPC ............. *C07F 7/20* (2013.01); *C07F 7/1804* (2013.01)

(58) Field of Classification Search
    None
    See application file for complete search history.

(56) References Cited

U.S. PATENT DOCUMENTS

| | | | |
|---|---|---|---|
| 6,608,225 B1 | 8/2003 | Larson et al. | |
| 6,815,554 B2 | 11/2004 | Pfeiffer et al. | |
| 8,476,375 B2 | 6/2013 | Backer et al. | |
| 8,580,886 B2 | 11/2013 | Backer et al. | |
| 8,692,012 B2 | 4/2014 | Daiss et al. | |
| 9,249,164 B2 | 2/2016 | Hupfield et al. | |
| 9,452,575 B2 | 9/2016 | Urushidani et al. | |
| 9,518,072 B2 | 12/2016 | Backer et al. | |
| 2012/0004437 A1 | 1/2012 | Stanjek et al. | |
| 2012/0283362 A1 | 11/2012 | Backer et al. | |
| 2013/0184482 A1* | 7/2013 | Hupfield | C07F 7/1892 556/442 |
| 2014/0011900 A1 | 1/2014 | Burns et al. | |
| 2014/0031487 A1 | 1/2014 | Guy et al. | |
| 2015/0126676 A1 | 5/2015 | Backer et al. | |

FOREIGN PATENT DOCUMENTS

WO    2016205648    12/2016

OTHER PUBLICATIONS

Osterholtz FD, et al. "Kinetics of the hydrolysis and condensation of organofunctional alkoxysilanes: a review", Journal of Adhesion Science and Technology, Taylor & Francis, GB, vol. 6, No. 1, 1992, pp. 127-149, XP008098738.
Search report from corresponding Japanese 2017-561626 application, dated Oct. 29, 2018.

\* cited by examiner

*Primary Examiner* — Clinton A Brooks
*Assistant Examiner* — Kofi Adzamli
(74) *Attorney, Agent, or Firm* — Catherine U. Brown

(57) ABSTRACT

A process for preparing an acryloyloxysilane, comprising: reacting a metal salt of a carboxylic acid having the formula $$[CR^2_2\!=\!CR^1CO^-]_aM^{a+} \qquad (I),$$

with a haloorganoalkoxysilane having the formula $$XR^3Si(OR^4)_nR^5_{3-n} \qquad (II)$$

at a temperature of from 50 to 160° C. and in the presence of a catalyst, and in the presence of water, an alcohol comprising 1 to 5 carbon atoms, or a combination of water and an alcohol comprising 1 to 5 carbon atoms, to form a mixture comprising an acryloyloxysilane and a metal halide having the formula $$M^{a+}X^-_a \qquad (III),$$

wherein $R^1$ is H, $R^7COO^-M^{a+}$, or $C_1$-$C_6$ hydrocarbyl, each $R^2$ is independently $R^1$ or $[COO^-]M^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$ and n is an integer from 1 to 3.

17 Claims, No Drawings

PROCESS FOR PREPARING AN ACRYLOYLOXYSILANE

CROSS-REFERENCE TO RELATED APPLICATIONS

This application is a U.S. national stage filing under 35 U.S.C. § 371 of PCT Application No. PCT/US16/038069 filed 17 Jun. 2016, currently pending, which claims the benefit of U.S. Provisional Patent Application No. 62/182169 filed 19 Jun. 2015 under 35 U.S.C. § 119 (e). PCT Application No. PCT/US16/038069 and U.S. Provisional Patent Application No. 62/182169 are hereby incorporated by reference.

FIELD OF THE INVENTION

The present invention relates to a process for preparing an acryloyloxysilane. More specifically, the present invention relates to processes for preparing acryloyloxysilanes comprising reacting a metal salt of an unsaturated carboxylic acid with a haloorganoalkoxysilane, in the presence of water, an alcohol, or water and an alcohol and a catalyst.

BACKGROUND OF THE INVENTION

Unsaturated organoalkoxysilanes containing an acryloyloxy group, such as 3-acryloyloxypropyltriethoxysilane, have been produced by the nucleophilic substitution reaction of a haloorganoalkoxysilane with a metal salt of an unsaturated carboxylic acid, such as sodium acrylate, in the presence of a suitable phase-transfer catalyst. In addition to the desired silane product, this process produces a metal halide precipitate as a by-product, which is unwanted in the silane product and must be removed.

A portion of the metal halide precipitate has a fine particle size that does not settle into a distinct layer making decanting the product from the precipitate difficult on a commercial scale. In addition, washing with water would promote hydrolysis of the silane and formation of dispersions that are hard to separate. Thus, the metal halide is typically removed by filtration. However, to filter the fine particle size of the metal halide precipitate requires significant time, so filtration is a significant bottleneck in commercial scale production.

Therefore, there is a need for processes for producing acryloyloxysilanes that produces a metal halide by-product precipitate that is more easily and quickly removed from the organoalkoxysilane containing an acryloyloxy group by filtration.

BRIEF SUMMARY OF THE INVENTION

The process of the present invention is directed to processes for preparing acryloyloxysilanes comprising reacting a metal salt of a carboxylic acid having the formula $$[CR^2_2\!\!=\!\!CR^1COO^-]_a M^{a+} \qquad (I),$$

with a haloorganoalkoxysilane having the formula $$XR^3Si(OR^4)_n R^5_{3-n} \qquad (II)$$

at a temperature of from 50 to 160° C. and in the presence of a catalyst, and in the presence of water, an alcohol comprising 1 to 5 carbon atoms, or a combination of water and an alcohol comprising 1 to 5 carbon atoms, to form a mixture comprising an acryloyloxysilane and a metal halide having the formula $$M^{a+}X^-_a \qquad (III),$$

wherein $R^1$ is H, $R^7COO^-\ M^{a+}$, or $C_1$-$C_6$ hydrocarbyl, each $R^2$ is independently $R^1$ or $[COO^-]M^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$, $R^7$ is hydrocarbylene having from 1 to 6 carbon atoms, and n is an integer from 1 to 3.

The processes of the present invention produces an acryloyloxysilane. Further, the process of the present invention produces a coarse metal halide precipitate that requires less time to filter and that separates quickly from the acryloyloxysilane forming a distinct layer enabling efficient decanting of the acryloyloxysilane from the metal halide and/or filtration.

The acryloyloxysilane of the invention may be used as a coupling agent for unsaturated resin or polymer systems, an adhesion promoter at organic-inorganic interfaces, and as a surface modifier.

DETAILED DESCRIPTION OF THE INVENTION

The process of the invention is for preparing an acryloyloxysilane, the process comprising: reacting a metal salt of a carboxylic acid having the formula $$[CR^2_2\!\!=\!\!CR^1COO^-]_a M^{a+} \qquad (I),$$

with a haloorganoalkoxysilane having the formula $$XR^3Si(OR^4)_n R^5_{3-n} \qquad (II)$$

at a temperature of from 50 to 160° C. and in the presence of a catalyst, and in the presence of water, an alcohol comprising 1 to 5 carbon atoms, or a combination of water and an alcohol comprising 1 to 5 carbon atoms, to form a mixture comprising an acryloyloxysilane and a metal halide having the formula $$M^{a+}X^-_a \qquad (III),$$

wherein $R^1$ is H, $R^7COO^-M^{a+}$, or $C_1$-$C_6$ hydrocarbyl, each $R^2$ is independently $R^1$ or $[COO^-]M^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$ and n is an integer from 1 to 3.

The metal salt of an unsaturated carboxylic acid has the formula $$[CR^2_2\!\!=\!\!CR^1COO^-]_a M^{a+} \qquad (I).$$

Examples of alkali metal or alkaline earth metal cations represented by $M^{a+}$ include, but are not limited to, $Li^+$, $Na^+$, $K^+$, $Mg^{2+}$, and $Ca^{2+}$. In one embodiment, $M^{a+}$ is $Na^+$ or $K^+$.

The hydrocarbyl groups represented by $R^1$ and $R^2$ typically have from 1 to 6 carbon atoms, alternatively from 1 to 4 carbon atoms, alternatively from 1 to 3 carbon atoms. Acyclic hydrocarbyl groups containing at least three carbon atoms can have a branched or unbranched structure. Examples of hydrocarbyl groups include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl; cycloalkyl, such as cyclopentyl and cyclohexyl; aryl, such as phenyl; alkenyl, such as vinyl, allyl, and propenyl; and alkynyl, such as ethynyl and propynyl. In one embodiment, one $R^2$ group is hydrogen and one $R^2$ group is propenyl (i.e., $CH_3CHCH$—).

Examples of the metal salt of an unsaturated carboxylic acid include, but are not limited to, sodium acrylate, sodium methacrylate, sodium ethacrylate (i.e., sodium 2-methylenebutanoate), sodium crotonate, sodium isocrotonate, sodium sorbate, potassium acrylate, potassium methacrylate, potassium ethacrylate (i.e., potassium 2-methylenebutanoate), potassium crotonate, potassium isocrotonate, potassium sorbate, magnesium acrylate, magnesium methacrylate, magnesium ethacrylate, magnesium crotonate, magnesium isocrotonate, magnesium sorbate, calcium acrylate, calcium methacrylate, calcium ethacrylate, calcium crotonate, calcium isocrotonate, and calcium sorbate, monosodium fumarate, disodium fumarate, monosodium maleate, disodium maleate, monosodium itaconate, disodium itaconate, monopotassium fumarate, dipotassium fumarate, monopotassium maleate, dipotassium maleate, monopotassium itaconate, dipotassium itaconate.

Processes of preparing metal salts of unsaturated carboxylic acids are well known in the art, and many of these compounds are commercially available. For example, the metal salt of an unsaturated carboxylic acid may be prepared by adding an unsaturated carboxylic acid dropwise to a solution of NaOEt in ethanol while maintaining the temperature below 25° C. and then stirring for one hour.

The haloorganoalkoxysilane has the formula

$$XR^3Si(OR^4)_nR^5_{3-n} \quad (II),$$

where X is halo. Examples of halo atoms represented by X include —F, —Cl, —Br, and —I.

The hydrocarbylene groups represented by $R^3$ typically have from 1 to 6 carbon atoms, alternatively from 2 to 4 carbon atoms, alternatively 3 carbon atoms. Hydrocarbylene groups containing at least three carbon atoms can have a branched or unbranched structure. Examples of hydrocarbylene groups include, but are not limited to, methylene, ethylene, propylene, 1-methylethylene, butylene, 1-methylpropylene, 2-methylpropylene, 1,1-dimethylethylene, pentylene, 1-methylbutylene, 1-ethylpropylene, 2-methylbutylene, 3-methylbutylene, 1,2-dimethylpropylene, 2,2-dimethylpropylene, hexylene, or a similar hydrocarbylene group.

The hydrocarbyl groups represented by $R^4$ typically have from 1 to 10 carbon atoms, alternatively from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, the examples given for $R^1$ and $R^2$ above and alkyl, such as hexyl, heptyl, octyl, nonyl, and decyl; cycloalkyl, such as methylcyclohexyl; aryl, such as napthyl; alkaryl such as tolyl and xylyl; aralkyl, such as benzyl and phenylethyl; and aralkenyl, such as styryl and cinnamyl.

The hydrocarbyl groups represented by $R^5$ typically have from 1 to 6 carbon atoms, alternatively from 1 to 4 carbon atoms. Acyclic hydrocarbyl groups containing at least three carbon atoms can have a branched or unbranched structure. Examples of hydrocarbyl groups include, but are not limited to, the examples given for $R^1$ and $R^2$.

Examples of the haloorganoalkoxysilane of formula (II) include, but are not limited to, chloromethyldimethylmethoxysilane, chloromethyltrimethoxysilane, chloromethyltriethoxysilane, 3-chloropropyltrimethoxysilane, 3-chloropropyltriethoxysilane, 3-chloropropylmethyldimethoxysilane, 3-chloropropylmethyldiethoxysilane, 3-chloropropyldimethylmethoxysilane, 3-chloropropyldimethylethoxysilane, 3-chloropropylethyldimethoxysilane, 3-chloropropylethyldiethoxysilane, 3-bromopropyltrimethoxysilane, 3-bromopropyltriethoxysilane, 3-iodopropyltrimethoxysilane, 3-iodopropyltriethoxysilane. In one embodiment, the haloorganoalkoxysilane of formula (II) is 3-chloropropyltrimethoxy silane or 3-chloropropyltriethoxysilane.

Processes of preparing haloorganoalkoxysilanes are well known in the art; many of these compounds are commercially available.

The reacting is in the presence of water, an alcohol comprising 1 to 5 carbon atoms, or a combination of water and an alcohol comprising 1 to 5 carbon atoms. The water may be deionized or distilled water or may be water present in other reactants.

In one embodiment, the reacting is in the presence of an alcohol comprising from 1 to 5 carbon atoms, alternatively from 1 to 3 carbon atoms, alternatively 1 carbon atom. In one embodiment, the alcohol is according to the formula $R^7OH$, where $R^7$ is hydrocarbyl group comprising from 1 to 5 carbon atoms. Acyclic hydrocarbyl $R^7$ groups containing at least three carbon atoms can have a branched or unbranched structure.

Examples of hydrocarbyl groups represented by $R^7$ include, but are not limited to, alkyl, such as methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl.

The alcohol having from 1 to 5 carbon atoms may be a primary, secondary, or tertiary alcohol when possible; alternatively primary or secondary, alternatively primary. Examples of the alcohol having from 1 to 5 carbon atoms include, but are not limited to, methanol, ethanol, propanol, isopropanol, butanol, isobutanol, sec-butanol, pentanol, and isopentanol. In one embodiment, the alcohol is methanol. Alcohols suitable for the present invention are available commercially.

The catalyst is any catalyst known to function as a catalyst in the reaction between a metal salt of an unsaturated carboxylic acid and a haloorganoalkoxysilane to form an acryloyloxysilane, alternatively, the catalyst is a phase-transfer catalyst, wherein the phase transfer catalyst is any phase-transfer catalyst known to function as a solid-solution phase-transfer catalyst in the nucleophilic substitution reaction between a metal salt of an unsaturated carboxylic acid and a haloorganoalkoxysilane to form an acryloyloxysilane.

Examples of the catalysts includes, but are not limited to, phase-transfer catalyst that are amines, such as triethylamine, dimethylaniline, 1,8-diazabicyclo[5.4.0]undec-7-ene, 1,4-diazabicyclo[2.2.2]octane, and 1,5-diazabicyclo[4.3.0]-non-5-ene; quaternary ammonium compounds, such as tributylmethyl ammonium chloride, triethylcetyl ammonium bromide, didodecyl dimethyl ammonium chloride, distearyl dimethyl ammonium chloride, tricaprylmethyl ammonium chloride, ALIQUAT® 336 [tris(n-$C_8$- and $C_{10}$-alkyl)methyl ammonium chloride], trioctyl methyl ammonium chloride, tetrabutyl ammonium chloride or bromide, tetrapropylammonium bromide, tetrabutylammonium bromide, tetrabutylammonium chloride, tetrapentylammonium bromide, tetrahexylammonium bromide, tetraoctylammonium bromide, methyltributylammonium bromide, and methyltributylammonium chloride; and quaternary phosphonium compounds, such as tetra-n-butylphosphonium bromide, tetra-n-butylphosphonium chloride, methyltri-n-butylphosphonium chloride, methyltri-n-butylphosphonium bromide, n-butyltriphenylphosphonium bromide, n-butyltriphenylphosphonium bromide, n-butyltriphenylphosphonium chloride, methyltriphenylphosphonium chloride and methyltriphenylphosphonium bromide. In one embodiment, the phase-transfer catalyst is tetrabutyl ammonium chloride or bromide, methyltriphenylphosphonium chloride, n-butyltriphenylphosphonium bromide, or tetra-n-butylphosphonium bromide. In one embodiment, combinations of catalysts are used.

The catalyst, such as phase-transfer catalysts, are made by processes known in the art. Many of these compounds are available commercially.

The process of the invention may further comprise a co-catalyst; alternatively the process of the invention further comprises a co-catalyst, wherein the co-catalyst is metal salt, alternatively a metal salt with iodide, alternatively potassium iodide.

The process of the invention may, optionally, be carried out in the presence of one or more free-radical inhibitors. As used herein, "inhibitors" are compounds that inhibit free-radical polymerization reactions.

Examples of inhibitors include, but are not limited to, amines, such as ethylenediaminetetraacetic acid, aromatic amines, such as N,N'-p-phenylenediamine, N,N'-di-β-naphthyl-p-phenylenediamine, and phenothiazine, quinines, hydroquinones, such as hydroquinone monomethyl ether, sterically hindered phenols, such as 2,6-di-tertbutylphenol, 2,6-di-tert-butyl-4-methylphenol, 2,6-di-tert-butyl-4-(N,N-dimethylamino)methylphenol, and butylated hydroxytoluene, and stable free radicals.

The inhibitors are made by processes known in the art. Many of these inhibitors are available commercially.

The reacting may also optionally be conducted in the presense of a non-polar solvent, alternatively the reacting may be in the presence of a non-polar solvent. The non-polar solvent has a dielectric constant below 10, alternatively below 5, alternatively from 1 to 5. In one embodiment, the non-polar solvent is a hydrocarbon having a number of carbon atoms from 5 to 20, alternatively from 6 to 16, alternatively 6 to 13. In another embodiment, the non-polar solvent is a mixture of hydrocarbons where two or more of the hydrocarbons in the mixture have a number of carbon atoms from 5 to 20, alternatively from 6 to 16, alternatively 6 to 13.

In one embodiment, the non-polar solvent comprises hydrocarbons that are aromatic, non-aromatic, cyclic, acyclic, branched, or alicyclic; alternatively paraffinic, isoparaffinic, or a mixture of paraffinic and isoparaffinic; alternatively acyclic an non-aromatic. In one embodiment the non-polar solvent comprises a paraffinic or isoparaffinic hydrocarbon having from 5 to 20 carbon atoms, alternatively 6 to 16 carbon atoms, alternatively from 6 to 14 carbon atoms. In one embodiment, the non-polar solvent comprises less than 1% (w/w), alternatively less than 0.5% (w/w), alternatively less than 500 ppm (by weight) of aromatic hydrocarbon, based on the weight of all hydrocarbons present during the reacting.

The non-polar solvent has a boiling point from 50 to 250° C., alternatively from 60 to 240° C., alternatively from 65 to 230° C. Alternatively the non-polar solvent is a mixture of hydrocarbons comprising isoalkanes having from 5 to 20 carbon atoms, alternatively 6 to 18 carbon atoms, alternatively 6 to 13 carbon atoms, alternatively 8 to 14 carbon atoms.

The non-polar solvent of the process has a density less than 1.0 grams per milliliter (g/mL), alternatively from 0.6 to 0.9 grams per mL, alternatively from 0.65 to 0.75 g/mL, at 25° C.

Examples of the non-polar solvents include, but are not limited to, organic solvents such as mineral spirits, toluene, m-, o-, and p-xylene and mixtures thereof, n-pentane, n-hexane, n-heptane, cyclopentane, cyclohexane, cyclooctane, cyclohexane, cis-cyclooctene, tert-butyl methyl ether and di-n-butyl ether, isoalkanes and mixtures thereof such as those sold under the ISOPAR® trademark such as ISOPAR G FLUID. In one embodiment, the non-polar solvent is a mixture of hydrocarbons comprising 6 to 13 carbon atoms and a boiling point from 65 to 230° C. (sold under the trade name ISOPAR G FLUID), alternatively heptane, alternatively a mixture of paraffinic and isoparaffinic hydrocarbons comprising 6 to 13 carbon atoms and a boiling point from 65 to 230° C. (sold under the trade name ISOPAR® G FLUID), wherein the mixture comprises from 50 to 100%, alternatively from 80 to 99%, alternatively from 90 to 99%, alternatively from 90 to 98%, based on the total amount of non-polar solvent present for the reacting, of n-heptane.

The reactor for carrying out the reacting in the process of the invention can be any suitable reactor for reacting a metal salt of an unsaturated carboxylic acid with a haloorganoalkoxysilane in the presences of a phase-transfer catalyst. For example, a glass, round-bottom flask may be used.

In one embodiment, the reactants are added to the reactor in any order. Alternatively, the metal salt of the unsaturated carboxylic acid, catalyst, a portion of the haloorganoalkoxysilane, and, if present, alcohol, water, co-catalyst, inhibitors and non-polar solvent, are added to the reactor and heated; after heating, the remaining amount of haloorganoalkoxysilane is added to the reactor. Alternatively, 100% of each of the metal salt of the unsaturated carboxylic acid, catalyst, and, if present, alcohol, water, inhibitors and non-polar solvent, and a portion of the haloorganoalkoxysilane are added to the reactor and heated; after heating, the remaining amount of haloorganoalkoxysilane is added to the reactor. As used herein, "a portion" as used in reference to the haloorganoalkoxysilane means up to 75%, alternatively up to 50%, alternatively from 30% to 55% of the total molar amount of the haloorganoalkoxysilane to be added in the process. As used herein, "the remaining amount" as used in reference to the haloorganoalkoxysilane added in the process of the invention means the amount of haloorganoalkoxysilane remaining to be added to the process after subtracting the portion of haloorganoalkoxysilane already added to the reactor from the total molar amount of haloorganoalkoxysilane to be added to the process, alternatively up to 75%, alternatively up to 45%, alternatively up to 25%, based on the total molar amount of haloorganoalkoxysilane to be added to the process, of the haloorganoalkoxysilane.

The rate of addition of the reactants in the process may controlled. The haloorganoalkoxysilane may be gradually introduced to the reactor and to the metal salt of the unsaturated carboxylic acid to prevent unwanted exotherms and improve processing.

The reaction of the process is typically carried out at a temperature of from 50 to 160° C., alternatively from 80 to 140° C., alternatively from 80 to 130° C., alternatively from 80 to 100° C., alternatively from 85 to 95° C., and at a pressure from 0 to 1000 kPag, alternatively from 50 to 200 kPag, alternatively from 80 to 150 kPag, alternatively at atmospheric pressure. The reactants are typically combined as described above at ambient temperature and then the combination brought to the temperatures and pressures described above.

The reaction of the process of the invention is typically carried out until at least 50% (w/w) of the haloorganoalkoxysilane has reacted, alternatively until at least 80% of the haloorganoalkoxysilane has reacted, alternatively until from 90 to 100% of the haloorganoalkoxysilane has reacted. The progression of the reaction of the haloorganoalkoxysilane can be monitored by standard processes known in the art, for example by gas chromatography (GC).

Typically, the time required to carry out the reaction of the process is at least 30 minutes, alternatively from 60 to 6000 minutes, alternatively from 120 to 1000 minutes, alternatively from 600 to 720 minutes.

The molar ratio of the metal salt of the unsaturated carboxylic acid to the haloorganoalkoxysilane is typically from 0.5-1.5:1, alternatively from 0.9-1.1:1, alternatively from 1-1.05:1.

The phase-transfer catalyst may be used in a catalytic effective amount. As used herein, a "catalytic effective amount" is an amount that will catalyze the nucleophilic substitution reaction between the haloorganoalkoxysilane and the salt of an unsaturated carboxylic acid to produce an acryloyloxysilane. For example, a catalytic effective amount is at least 0.001% (w/w), alternatively from 0.005 to 0.5%, alternatively from 0.01 to 0.05% (w/w), based on the combined weight of the phase-transfer catalysts, the haloorganoalkoxysilane, the salt of an unsaturated carboxylic acid, and the mineral spirits.

In one embodiment the reacting is in the presence of water, alternatively in the presence of at least 100 ppmw, alternatively at least 2000 ppw, alternatively from 100 to 2400 ppmw, alternatively from 3500 to 5000 ppmw, based on the weight of all materials in the reaction, of water. The amount of water in the reaction is produced by processes known in the art, considering the amount of water contributed by all the materials in the reaction with the balance desired produced by adding additional water if the amount for the other ingredients is less than the desired amount, or by removing water from one or more of the materials in the reaction by methods known in the art if the amount of water is more than desired.

In one embodiment, the reacting is conducted in the presence of the alcohol described above, alternatively at least 80 ppmw, alternatively from 80 to 6400 ppmw, alternatively from 80 to 4800 ppmw, based on the weight of alcohol and all other materials in the reaction, of the alcohol described above. The amount of alcohol in the reaction is produced by processes known in the art, considering the amount of alcohol contributed by all the materials in the reaction with the balance desired produced by adding additional alcohol if the amount for the other ingredients is less than the desired amount, or by removing alcohol from one or more of the materials in the reaction by methods known in the art if the amount of alcohol is more than desired.

In one embodiment, the reacting is conducted in the presence of water and the alcohol described above, alternatively in the presence of from 100 to 5000 ppmw water and from 80 to 6400 ppmw alcohol, alternatively from 100 to 1200 ppmw of water and from 80 to 4800 ppmw alcohol, alternatively from 1000 ppm water to 4800 ppmw of water, and from 80 to 1000 ppmw of alcohol, alternatively from 400 to 800 ppmw of water, and from 4500 to 5000 ppmw alcohol, alternatively from 2100 to 3500 ppmw of water, and from 3100 to 3500 ppmw methanol, where ppmw is calculated based on the weight of all materials in the reaction. The amount of water and alcohol present is achieved in the same way as described above for the individual materials.

When included, the inhibitor is typically from 1 to 10,000 ppmw, alternatively from 10 to 2500 ppmw, alternatively from 1800 to 2400 ppmw, based on the combined weight of the inhibitor, the haloorganoalkoxysilane, the metal salt of the unsaturated carboxylic acid, and the alcohol.

The non-polar solvent may be present in the reaction of the process of the invention at from 10 to 90% (w/w), alternatively 15 to 80% (w/w), alternatively from 25 to 60% (w/w), based upon the combined weight of the non-polar solvent, the acryloyloxysilane, and the metal halide.

The co-catalyst is present in a catalytic effective amount. A catalytic effective amount as used herein with respect to the co-catalyst is an amount sufficient to act as a co-catalyst in the reaction of the metal salt of the carboxylic acid and the haloorganoalkoxysilane, alternatively a catalytic effective amount is in a ratio to the catalyst from 0.01 to 10 (catalyst/co-catalysts), alternatively from 0.1 to 5, alternatively from 0.25 to 2, alternatively from 0.4 to 1.1.

The reaction of the process of the invention is typically carried out in an inert gas atmosphere; however, it may be carried out in air. The inert gas is a gas that is unreactive toward the components present in the reaction mixture under reaction conditions. Examples of inert gases are nitrogen and argon.

The reaction forms a mixture comprising an acryloyloxysilane, and a metal halide having the formula

$$M^{a+}X^-{}_a \qquad (III),$$

wherein $X^-$ is a halide anion. As used herein, "acryloyloxysilane" is intended to include materials that may not necessarily be named an acryloyloxysilane according to the formula, but includes the acryloyloxy functionality. For example, it is contemplated that acryloyloxy may include sorbyloxy functional groups.

The acryloyloxysilane has the formula

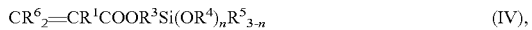

$$CR^6{}_2{=}CR^1COOR^3Si(OR^4)_nR^5{}_{3-n} \qquad (IV),$$

wherein each $R^1$, $R^3$, $R^4$, $R^5$, and n is independently as described above for the haloorganoalkoxysilane and the metal salt of a carboxylic acid, and each $R^6$ is independently H, $C_1$-$C_6$ hydrocarbyl, or $COOR^3Si(OR^4)_nR^5{}_{3-n}$, wherein each $R^3$, $R^4$, $R^5$, and n is independently as described above for the haloorganoalkoxysilane and the metal salt of a carboxylic acid.

Examples of the acryloyloxysilane include, but are not limited to, sorbyloxymethyldimethylmethoxysilane, γ-sorbyloxypropylmethydimethoxysilane, γ-sorbyloxypropyltrimethoxysilane, γ-sorbyloxypropyltriethoxysilane, γ-sorbyloxybutyldimethoxysilane, methacryloyloxymethyldimethylmethoxysilane, γ-methacryloyloxypropylmethydimethoxysilane, γ-methacryloyloxypropyltrimethoxysilane, γ-methacryloyloxypropyltriethoxysilane, γ-methacryloyloxybutyldimethoxysilane, δ-methacryloyloxybutyltrimethoxysilane, δ-methacryloyloxybutylmethyldimethoxysilane, acryloyloxymethyldimethylmethoxysilane, γ-acryloyloxypropylmethyldimethoxysilane, γ-acryloyloxypropyltrimethoxysilane, γ-acryloyloxypropyltriethoxysilane, γ-acryloyloxypropylbutyldimethoxysilane, δ-acryloyloxybutyltrimethoxysilane, δ-acryloyloxybutylmethyldimethoxysilane, bis(γ-trimethoxysilylpropyl) fumarate, bis(γ-triethoxysilylpropyl) fumarate, bis(γ-trimethoxysilylpropyl) maleate, bis(γ-triethoxysilylpropyl) maleate, bis(γ-trimethoxysilylpropyl) itaconate, bis(γ-triethoxysilylpropyl) itaconate.

The metal halide is according to the formula

$$M^{a+}X^-{}_a \qquad (III),$$

wherein M and a are as defined and exemplified above for the metal salt of the unsaturated carboxylic acid, and $X^-$ is a halide anion. Examples of halide anions include chloride, bromide, fluoride and iodide. Examples of the metal halide include, but are not limited to sodium chloride, sodium bromide, sodium iodide, potassium chloride, potassium bromide, potassium iodide, magnesium chloride, magnesium bromide, magnesium iodide, calcium chloride, calcium bromide, and calcium iodide.

The process of the invention may also comprise removing at least a portion of the metal halide from the mixture. As used herein, "a portion" means enough to reduce the metal halide in the acryloyloxysilane to within the ranges described below. For example, a portion is typically at least 50%, alternatively at least 90%, alternatively at least 99.99%, of the initial amount of the metal halide in the mixture.

The metal halide may be removed from the mixture by processes known in the art for removing a solid metal halide from an organic material. The metal halide may be removed by, for example, filtration, decantation, washing, or a combination of filtration, decantation and washing. In one embodiment, the metal halide is removed by filtration or decantation. In another embodiment, the metal halide is removed by decanting the acryloyloxysilane from the metal halide followed by washing, as described and exemplified below in the second process of the invention, the metal halide with a brine solution.

After the step of removing at least a portion of the metal halide from the mixture, the acryloyloxysilane typically has less than 10,000 parts per million by weight (ppmw), alternatively from 1 to 1000 ppmw, alternatively from 10 to 100 ppmw, based on the weight of the acryloyloxysilane, of the metal halide.

The process of the invention may further comprise recovering the acryloyloxysilane. The recovering acryloyloxysilane may be accomplished by processes known in the art, for example by distillation.

The processes of the present invention produce acryloyloxysilanes. Further, the processes of the present invention produce a metal halide precipitate that requires less time to filter. Not wishing to be bound by theory, it is believed that the faster filtration is due to the precipitate having larger particle size than precipitates made from processes not according to the present invention. Still further, the processes of the present invention produce a metal halide precipitate that settles quickly forming a distinct layer enabling efficient separation of the acryloyloxysilane from the metal halide by decantation or filtration.

The acryloyloxysilane of the invention may be used as a coupling agent for unsaturated resin or polymer systems, an adhesion promoter at organic-inorganic interfaces, and as a surface modifier.

EXAMPLES

The following examples are presented to better illustrate the method of the present invention, but are not to be considered as limiting the invention, which is delineated in the appended claims. Unless otherwise noted, all parts and percentages reported in the examples are by weight. The following table describes the abbreviations used in the examples:

TABLE 1

List of abbreviations used in the examples.

| Abbreviation | Word |
| --- | --- |
| g | gram |
| Me | methyl |
| wt | weight |
| % | percent |
| mol | mole |
| mmol | millimole |
| hr | hour |
| °C. | degrees Celsius |
| NA | Not Applicable |
| mL | milliliters |
| solids content | (wt. of dried sample/wt. of initial sample) × 100 and determined as described below |
| rpm | revolutions per minute |
| ppmw | parts per million by weight |
| PTZ | Phenothiazine |
| BHT | butylated hydroxytoluene |
| NaOEt | sodium ethoxylate |
| TBAB | tetrabutylammonium bromide |
| DBU | 1,8-diazabicyclo[5.4.0]undec-7-ene |
| CPTES | γ-chloropropyltriethoxysilane |
| g-ATE | γ-acryloyloxypropyltriethoxysilane |
| yield | (isolated wt. of organoalkoxysilane product/theoretical wt. of organoalkoxysilane product) × 100 |
| PTC | Phase-transfer catalysis |
| EDTA-NA | ethylenediaminetetraacetic acid disodium salt |
| CPTMS | γ-chloropropyltrimethoxysilane |
| g-STM | γ-sorbyloxypropyltrimethoxysilane |
| g-ATM | γ-acryloyloxypropyltrimethoxysilane |
| % organic recovery rate | (isolated organics/theoretical weight of organics) × 100 |
| organics | organoalkoxysilane product and non-polar solvent |
| Isopar G | Isopar G Fluid is produced from petroleum-based raw materials which are treated with hydrogen in the presence of a catalyst to produce a low odor, low aromatic hydrocarbon solvent. The major components are isoalkanes. CAS No: 64742-48-9. Also called hydrotreated light steam cracked naptha. |

Example 1

A jacketed 5 L baffled reactor equipped with a mechanical agitator, thermometer, and condenser was loaded with 980 g Isopar G, 1000 g potassium sorbate, and 1320 g CPTMS. The stabilizers PTZ (2.4 g), BHT (2.3 g), and EDTA-Na$_4$ (2.3 g), and TBAB (36.5 g) were added sequentially. After allowing the contents of the reactor to mix for 10 min., water was added for some of the examples as shown in Table 1. Methanol was also added in varying amount as indicated in Table 1. This was accomplished by either distilling the CPTM to reduce methanol from an initial value of 0.84% methanol or by adding additional methanol to the CPTMS. CPTMS with the desired methanol concentration was added to the reactor to achieve the desired overall methanol concentration as shown in Table 1. After heating the reactor to the temperature set point, the temperature was held constant for 5 to 10 hours at atmospheric pressure until the reaction was complete. The time required to complete the reaction varied depending on methanol and water concentration as well as temperature. The contents of the reaction were then filtered using a pressure filter to remove potassium chloride. The same procedure and equipment, including filtration equipment, was used with all runs in Table 1 except for variation in methanol and water concentration and reaction temperature as shown in Table 1.

TABLE 1

| Run | Water (PPM) | Methanol (PPM) | Reaction Temperature (° C.) | g-STM Yeild (%) | Filtration Rate (g/min) |
|---|---|---|---|---|---|
| 1 | 490 | 3300 | 105 | 95 | 49 |
| 2 | 790 | 3300 | 105 | 93 | 66 |
| 3 | 1100 | 3300 | 105 | 90 | 95 |
| 4 | 2100 | 3300 | 105 | 87 | 103 |
| 5 | 3500 | 3300 | 105 | 73 | 103 |
| 6 | 725 | 80 | 105 | 92 | 41 |
| 7 | 725 | 1900 | 105 | 87 | 65 |
| 8 | 725 | 2500 | 105 | 87 | 82 |
| 9 | 725 | 4800 | 105 | 89 | 117 |
| 10 | 725 | 5600 | 105 | 90 | 98 |
| 11 | 725 | 6400 | 105 | 90 | 38 |
| 12 | 725 | 3300 | 85 | 88 | 99 |
| 13 | 725 | 3300 | 95 | 94 | 88 |
| 14 | 725 | 3300 | 105 | 93 | 84 |
| 15 | 725 | 3300 | 115 | 89 | 31 |

That which is claimed is:

1. A process for preparing an acryloyloxysilane, the process comprising:
   1) heating, at a temperature of from 50 to 115° C.
   a metal salt of a carboxylic acid having the formula $$[CR^2{}_2=CR^1COO^-]_aM^{a+} \quad (I),$$

a haloorganoalkoxysilane having the formula $$XR^3Si(OR^4)_nR^5{}_{3-n} \quad (II),$$

a catalyst, and
      a combination of 2100 to 3500 ppmw water and 3100 to 3500 ppmw methanol, to form a mixture comprising an acryloyloxysilane and a metal halide having the formula $$M^{a+}X^-_a \quad (III),$$

wherein $R^1$ is H, $R^7COO^-M^{a+}$, or $C_1$-$C_6$ hydrocarbyl, each $R^2$ is independently $R^1$ or $[COO^-]M^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$, $R^7$ is hydrocarbylene having from 1 to 6 carbon atoms, and n is an integer from 1 to 3; and
   2) removing at least a portion of the metal halide from the mixture by filtration.

2. The process of claim 1, wherein the acryloyloxysilane has the formula $$CR^6{}_2=CR^1COOR^3Si(OR^4)_nR^5{}_{3-n} \quad (IV),$$

wherein $R^1$, $R^3$, $R^4$, $R^5$, and n are as defined in claim 1, and wherein each $R^6$ is independently H, $C_1$-$C_6$ hydrocarbyl, or $COOR^3Si(OR^4)_nR^5{}_{3-n}$, wherein $R^3$, $R^4$, $R^5$, and n are as defined in claim 1.

3. The process of claim 1, wherein $M^{a+}$ is a sodium ion or potassium ion, a is 1, and X is chloro.

4. The process of claim 1, wherein each $R^1$ is independently H, methyl, or $[CH_2COO^-]M^{a+}$, each $R^2$ is independently H, methyl, or $[COO^-]M^{a+}$, $R^3$ is methylene, ethylene, or propylene, each $R^4$ is independently methyl or ethyl, each $R^5$ is independently H, methyl, or ethyl, $R^7$ is methylene, ethylene, or propylene, and n is 3.

5. The process of claim 1, wherein the catalyst is tetrabutylammonium bromide.

6. The process of claim 1, wherein the metal salt of a carboxylic acid is selected from the metal salt fumaric acid, sorbic acid, or acrylic acid.

7. The process of claim 1 wherein the acryloyloxysilane is γ-acryloyloxypropylmethyldimethoxysilane, γ-acryloyloxypropyltrimethoxysilane, γ-sorbyloxypropylmethyldimethoxysilane, γ-sorbyloxypropyltrimethoxysilane, γ-acryloyloxypropyltriethoxysilane, γ-sorbyloxypropyltriethoxysilane, bis(γ-trimethoxysilylpropyl) fumarate, or bis (γ-triethoxysilylpropyl) fumarate.

8. The process of claim 1, wherein the heating is done in the presence of a non-polar solvent, wherein the non-polar solvent comprises a hydrocarbon having from 5 to 20 carbon atoms.

9. The process of claim 8, wherein the non-polar solvent comprises less than 5% aromatic compounds.

10. The process of claim 1, wherein heating is conducted in a reactor, wherein the metal salt of the unsaturated carboxylic acid, catalyst, a portion of the haloorganoalkoxysilane, and, if present, alcohol, water, co-catalyst, inhibitors and non-polar solvent, are added to the reactor and heated, and wherein after the heating, the remaining amount of haloorganoalkoxysilane is added to the reactor.

11. A process for preparing an acryloyloxysilane, the process comprising:
   1) heating, at a temperature of from 50 to 160° C.
   a metal salt of a carboxylic acid having the formula $$[CR^2{}_2=CR^1COO^-]_aM^{a+} \quad (I),$$

a haloorganoalkoxysilane having the formula $$XR^3Si(OR^4)_nR^5{}_{3-n} \quad (II),$$

a catalyst, and one of
      i) a combination of 400 ppmw to 3,500 ppmw water and 4500 to 5600 ppmw methanol, or
      ii) a combination of 1100 to 3500 ppmw water and 3100 to 3500 ppwm methanol,
   to form a mixture comprising an acryloyloxysilane and a metal halide having the formula $$M^{a+}X^-_a \quad (III),$$

wherein $R^1$ is H, $R^7COO^-M^{a+}$, or $C_1$-$C_6$ hydrocarbyl, each $R^2$ is independently $R^1$ or $[COO^-]M^{a+}$, $M^{a+}$ is an alkali metal cation or alkaline earth metal cation, a is 1 or 2, X is halo, $R^3$ is $C_1$-$C_6$ hydrocarbylene, each $R^4$ is independently $C_1$-$C_{10}$ hydrocarbyl, each $R^5$ is independently $R^1$, $R^7$ is hydrocarbylene having from 1 to 6 carbon atoms, and n is an integer from 1 to 3; and
   2) removing at least a portion of the metal halide from the mixture by filtration.

12. The process of claim 11, wherein $M^{a+}$ is a sodium ion or potassium ion, a is 1, and X is chloro.

13. The process of claim 11, wherein each $R^1$ is independently H, methyl, or $[CH_2COO^-]M^{a+}$, each $R^2$ is independently H, methyl, or $[COO^-]M^{a+}$, $R^3$ is methylene, ethylene, or propylene, each $R^4$ is independently methyl or ethyl, each $R^5$ is independently H, methyl, or ethyl, $R^7$ is methylene, ethylene, or propylene, and n is 3.

14. The process of claim 11, wherein the catalyst is tetrabutylammonium bromide.

15. The process of claim 11, wherein the metal salt of a carboxylic acid is selected from a metal salt of fumaric acid, sorbic acid, or acrylic acid.

16. The process of claim 11, wherein the acryloyloxysilane is γ-acryloyloxypropylmethyldimethoxysilane, γ-acryloyloxypropyltrimethoxysilane, γ-sorbyloxypropylmethyldimethoxysilane, γ-sorbyloxypropyltrimethoxysilane, γ-acryloyloxypropyltriethoxysilane, γ-sorbyloxypropyltriethoxysilane, bis(γ-trimethoxysilylpropyl) fumarate, or bis (γ-triethoxysilylpropyl) fumarate.

17. The process of claim 11, wherein the heating is done in the presence of a non-polar solvent, wherein the non-polar solvent comprises a hydrocarbon having from 5 to 20 carbon atoms.

* * * * *